United States Patent
Li et al.

(10) Patent No.: US 11,059,034 B2
(45) Date of Patent: Jul. 13, 2021

(54) ALKYLAROMATIC CONVERSION CATALYST

(71) Applicant: SHELL OIL COMPANY, Houston, TX (US)

(72) Inventors: Hong-Xin Li, Lansdale, PA (US); Gisela Sabater Pujadas, Amsterdam (NL); Ingrid Maria Van Vegchel, Amsterdam (NL); Yuriy Yanson, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/339,623

(22) PCT Filed: Oct. 4, 2017

(86) PCT No.: PCT/EP2017/075238
§ 371 (c)(1),
(2) Date: Apr. 4, 2019

(87) PCT Pub. No.: WO2018/065474
PCT Pub. Date: Apr. 12, 2018

(65) Prior Publication Data
US 2019/0232262 A1 Aug. 1, 2019

Related U.S. Application Data

(60) Provisional application No. 62/404,819, filed on Oct. 6, 2016.

(51) Int. Cl.
| | | |
|---|---|---|
| *C07C 4/18* | (2006.01) | |
| *B01J 29/44* | (2006.01) | |
| *B01J 35/02* | (2006.01) | |
| *B01J 37/02* | (2006.01) | |
| *C07C 5/27* | (2006.01) | |
| *B01J 37/04* | (2006.01) | |
| *B01J 23/62* | (2006.01) | |
| *B01J 29/80* | (2006.01) | |
| *B01J 35/00* | (2006.01) | |
| *B01J 29/40* | (2006.01) | |
| *B01J 35/10* | (2006.01) | |
| *B01J 37/00* | (2006.01) | |
| *B01J 37/08* | (2006.01) | |
| *C01B 39/38* | (2006.01) | |

(52) U.S. Cl.
CPC ............ *B01J 29/44* (2013.01); *B01J 23/626* (2013.01); *B01J 29/40* (2013.01); *B01J 29/80* (2013.01); *B01J 35/002* (2013.01); *B01J 35/0006* (2013.01); *B01J 35/023* (2013.01); *B01J 35/1014* (2013.01); *B01J 35/1019* (2013.01); *B01J 35/1038* (2013.01); *B01J 37/0018* (2013.01); *B01J 37/0201* (2013.01); *B01J 37/0236* (2013.01); *B01J 37/04* (2013.01); *B01J 37/08* (2013.01); *C01B 39/38* (2013.01); *C07C 4/18* (2013.01); *C07C 5/2708* (2013.01); *B01J 2229/16* (2013.01); *B01J 2229/37* (2013.01); *C01P 2002/60* (2013.01); *C01P 2006/12* (2013.01); *C01P 2006/14* (2013.01); *C07C 2529/44* (2013.01); *Y02P 20/52* (2015.11)

(58) Field of Classification Search
CPC ... B01J 29/40; B01J 29/44; B01J 29/80; B01J 35/0006; B01J 35/002; B01J 35/023; B01J 35/1014; B01J 35/1019; B01J 35/1038; B01J 23/626; B01J 37/0009; B01J 37/0018; B01J 37/0201; B01J 37/0236; B01J 37/04; B01J 37/08; B01J 2229/16; B01J 2229/37; C07C 5/2708; C07C 4/18; C07C 2529/44; C07C 15/04; C07C 15/067; C01B 39/38; Y02P 20/52; C01P 2006/12; C01P 2006/14; C01P 2002/60

See application file for complete search history.

(56) References Cited

U.S. PATENT DOCUMENTS

| | | | |
|---|---|---|---|
| 4,753,910 A | | 6/1988 | Han et al. |
| 5,516,956 A | * | 5/1996 | Abichandani ............ B01J 29/44 585/481 |

(Continued)

FOREIGN PATENT DOCUMENTS

| | | |
|---|---|---|
| RU | 2256640 C1 | 7/2005 |
| WO | 2006022991 A1 | 3/2006 |
| WO | 2013032630 A2 | 3/2013 |

OTHER PUBLICATIONS

International Search Report and Written Opinion received for PCT Patent Application No. PCT/EP2017/075238, dated Dec. 1, 2017, 10 pages.

*Primary Examiner* — Youngsul Jeong
*Assistant Examiner* — Jason Y Chong
(74) *Attorney, Agent, or Firm* — Charles W. Stewart

(57) ABSTRACT

Process for dealkylation of alkylaromatic compounds which process comprises contacting an alkylaromatic feedstock with i) a first catalyst comprising a) a carrier comprising of from 20 to 70 wt. % of refractory oxide binder and of from 30 to 80 wt. % of dealuminated ZSM-5 having a crystallite size of from 500 to 10,000 nm and a silica to alumina molar ratio (SAR) of from 20 to 100; b) of from 0.001 to 5 wt. % metal chosen from the group consisting of Groups 6, 9 and 10; and optionally c) up to 0.5 wt. % of a Group 14 metal, and ii) a subsequent catalyst comprising a) a carrier comprising of from 20 to 70 wt. % of refractory oxide binder and of from 30 to 80 wt. % of ZSM-5 having a crystallite size of from 3 to 100 nm and a SAR of from 20 to 200; b) of from 0.001 to 5 wt. % of metal chosen from the group consisting of Groups 6, 9 and 10; and optionally c) up to 0.5 wt. % of a Group 14 metal.

8 Claims, No Drawings

(56) References Cited

U.S. PATENT DOCUMENTS

| | | | |
|---|---|---|---|
| 6,028,238 A | 2/2000 | Beck et al. | |
| 6,518,472 B1 | 2/2003 | Feinstein et al. | |
| 6,930,217 B2 | 8/2005 | Shan et al. | |
| 7,411,103 B2 * | 8/2008 | Schmidt | C07C 5/2737 |
| | | | 585/481 |
| 8,574,542 B2 | 11/2013 | Domokos et al. | |
| 9,233,886 B2 | 1/2016 | Adam et al. | |
| 2010/0217057 A1 * | 8/2010 | Domokos | B01J 29/44 |
| | | | 585/488 |
| 2010/0249479 A1 | 9/2010 | Berg-Slot et al. | |
| 2013/0217936 A1 | 8/2013 | Cheng et al. | |

* cited by examiner

ALKYLAROMATIC CONVERSION CATALYST

CROSS REFERENCE TO RELATED APPLICATIONS

This is a national stage application of International Application No. PCT/EP2017/075238, filed 4 Oct. 2017, which claims benefit of priority to U.S. Patent Application No. 62/404,819, filed 6 Oct. 2016.

The present invention relates to an alkylaromatic conversion catalyst, its preparation, and its use in ethylbenzene dealkylation.

BACKGROUND OF THE INVENTION

Ethylbenzene (EB) is one of the aromatic hydrocarbons that can be obtained from naphtha pyrolysis or reformate. Reformate is an aromatic product obtained by the catalyzed conversion of straight-run hydrocarbons boiling in the 70 to 190° C. range, such as straight-run naphtha. The catalysts used for the production of reformate are often platinum-on-alumina catalysts. The reformate feedstock itself is obtained by fractionation or distillation of crude petroleum oil, its composition varying depending on the source of the crude oil, but generally having a low aromatics content. On conversion to reformate, the aromatics content is considerably increased and the resulting hydrocarbon mixture becomes highly desirable as a source of valuable chemical intermediates and as a component for gasoline. The principle components are a group of aromatics often referred to as BTX: benzene, toluene and the xylenes, including ethylbenzene. Other components may be present such as their hydrogenated homologues, e.g. cyclohexane.

Of the BTX group, the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity and xylene isomerisation or transalkylation processes have been developed to increase the proportion of para-xylene. A further process that can be applied is the hydrodealkylation of ethylbenzene to benzene.

Generally, it is preferred to isolate BTX from the reformate stream, and subject the BTX stream to xylene isomerisation with the aim of maximising the para-xylene component. Xylene isomerisation is a catalytic process. Some catalysts used in this process have the ability to not just isomerise xylenes but to simultaneously dealkylate the ethylbenzene component. It is desirable for such catalysts to be optimized to achieve attractive concentrations of para-xylene in the product mixture at high EB conversion.

Normally the para-xylene is then separated out to leave benzene, toluene (unless one or more toluene conversion processes have already been applied) and the remaining mixed xylenes, including ethylbenzene. This BTX stream can either be converted by reforming to increase the yield of xylenes by converting ethylbenzene to xylenes and isomerize xylene isomers to equilibrium concentrations or can be converted by dealkylation to selectively eliminate ethylbenzene to increase the yield of benzene while allowing the xylene isomers to reach equilibrium concentrations.

Some prior art documents describe dual-catalyst systems for use in the processing of BTX, in particular for the dealkylation of ethylbenzene and isomerization of xylenes.

For example, U.S. Pat. No. 5,516,956 A describes a process for isomerizing xylenes in a feed containing ethylbenzene and xylenes using a first catalyst bed comprising a silica binder and an intermediate pore size zeolite which zeolite has been modified by being exposed to at least one selectivation sequence in the presence of a selectivating agent, in particular, a Si-containing selectivating agent and a second catalyst bed comprising an intermediate pore size zeolite. Examples of suitable zeolites are said to include ZSM-5, ZSM-11, ZSM-12, ZSM-21, ZSM-22, ZSM-23, ZSM-35, ZSM-38, ZSM-48, ZSM-57 and ZSM-58.

U.S. Pat. No. 6,028,238 A also describes a dual catalyst system for use in isomerizing a feed containing ethylbenzene and xylene. In a first stage, the feed is contacted under ethylbenzene conversion conditions with a particulate first catalyst comprising a molecular sieve having a constraint index of 1-12 and particles having a surface to volume ratio of about 80 to less than 200 inch-1 to convert ethylbenzene in the feed to form an ethylbenzene-depleted product; and then, in a second stage, the ethylbenzene-depleted product is contacted under xylene isomerization conditions with a second catalyst component. Preferably, the molecular sieve of the first catalyst has an average crystal size in excess of 100 nm (>0.1 micron) and the molecular sieve of the second catalyst has an average crystal size of less than 100 nm (<0.1 micron). The first catalyst may be selectivated with silica using an organosilicon compound.

WO 2006/022991 A1 describes a two-component catalyst system comprising a first component effective for converting ethylbenzene and comprising a first molecular sieve having a Constraint Index of about 1 to about 12 and an effective amount of a Group VIII metal; and a second component effective for isomerising xylenes and comprising a second molecular sieve having a Constraint Index of about 1 to about 12 and an effective amount of a Group VIII metal. In order to achieve higher diffusivity, the first component is selectivated by deposition on the surface of the catalyst particles of a layer of coke and/or an oxide, such as silica (for example, by conducting one or more treatments with an organosilicon compound).

WO 2013/032630 A2 discloses that the catalyst system of U.S. Pat. No. 6,028,238 A has disadvantages as in commercial operation, there can be large start-up exotherms during the initial oil-in period (contact of the catalyst with feed).

WO 2013/032630 A2 presents a process for the improved manufacture of para-xylene from a C8 aromatic hydrocarbon stream by a process that is said to include mitigation of large exotherms at the start-up of said process by sulfiding of the catalysts in the system prior to contact with the feed ("pre-sulfiding").

U.S. Pat. No. 6,518,472 B1 describes a triple catalyst system for the isomerization of a xylene and conversion of ethylbenzene comprising a first catalyst having activity for the conversion of ethylbenzene, a second catalyst having hydrogenation activity, and a third catalyst having activity for the isomerisation of a xylene.

However, whilst dual and triple catalyst systems have been described in the art, there is a continued need to develop catalyst systems for use in the combined dealkylation of ethylbenzene and isomerization of xylenes which not only demonstrate advantageous xylene isomerization in combination with high ethylbenzene conversion, but which also can be manufactured without the need for selectivation pretreatment using organosilicon compounds or coke deposition, which are complicated and costly procedures and which can affect catalyst performance by causing pore blockages.

SUMMARY OF THE INVENTION

The present invention provides a process for dealkylation of alkylaromatic compounds which process comprises contacting an alkylaromatic feedstock with i) a first catalyst comprising a) a carrier which comprises of from 20 to 70% by weight (wt. %) of a refractory oxide binder and of from 30 to 80 wt. % of dealuminated ZSM-5 having a crystallite size of from 500 to 10,000 nm and a silica to alumina molar ratio in the range of from 20 to 100; b) an amount of from 0.001 to 5 wt. % of one or more metals chosen from the group consisting of Groups 6, 9 and 10; and optionally c) a metal chosen from Group 14 in an amount up to 0.5 wt. %, and ii) a subsequent catalyst comprising a) a carrier which comprises of from 20 to 70 wt. % of a refractory oxide binder; of from 30 to 80 wt. % of ZSM-5 having a crystallite size of from 3 to 100 nm and a silica to alumina molar ratio in the range of from 20 to 200; b) an amount of from 0.001 to 5 wt. % of one or more metals chosen from the group consisting of Groups 6, 9 and 10; and optionally c) a metal chosen from Group 14 in an amount up to 0.5 wt. %.

All weight amounts, as the term is used in relation with the catalyst composition or the catalyst preparation, are based on the basis of total catalyst and on dry amounts. Any water and other solvent present in the starting compounds is to be disregarded.

The crystallite size is measured by Transmission Electron Microscopy (TEM) with the average based on the number average.

Groups 6, 9, 10 and 14 are as defined in the IUPAC Periodic Table of Elements dated 1 May 2013.

The weight amounts of metal are calculated as amount of metal on total weight of catalyst independent of the actual form of the metal.

The bulk or overall SAR can be determined by any one of a number of chemical analysis techniques. Such techniques include X-ray fluorescence, atomic adsorption, and inductive coupled plasma-atomic emission spectroscopy (ICP-AES). All will provide substantially the same bulk ratio value. The silica to alumina molar ratio for use in the present invention is determined by X-ray fluorescence.

DETAILED DESCRIPTION OF THE INVENTION

It is an aim of the present invention to provide a process that will dealkylate an alkylaromatics feedstock. It is desirable if additionally xylene isomers isomerize thereby increasing the amount of para-xylene in the product obtained.

The product of the present process was observed to have a high degree of equilibrium concentration of para-xylene. This was especially surprising as the relatively small ZSM-5 particles of the subsequent catalyst provide more surface area without steric hindrance thereby potentially allowing for side-reactions.

The ZSM-5 for use in the first catalyst has a silica to alumina molar ratio (SAR) in the range of from 20 to 100, preferably of at least 25, most preferably at least 30, and is preferably at most 100, most preferably at most 90, especially at most 50. Most preferably, the SAR is of from 35 to 50.

Most preferably, the ZSM-5 for use in the first catalyst of the present invention is prepared by synthesis from an aqueous reaction mixture comprising an alumina source, a silica source, an alkali source and L-tartaric acid or a water-soluble salt thereof. Full details on ZSM-5 which preferably is used in the present invention are described in U.S. Pat. No. 8,574,542 B2.

The crystallite size of the ZSM-5 of the first catalyst preferably is of from 500 nm to 10,000 nm. More specifically, the size of the ZSM-5 crystal of the first catalyst is at least 1,000 nm.

The first catalyst comprises dealuminated ZSM-5. Dealuminated ZSM-5 has a lower concentration of alumina at the surface than ZSM-5 which has not been dealuminated. Dealumination can be carried out either on the zeolite per se or on zeolite which has been incorporated into extrudates. In many cases, it is preferred to dealuminate the extrudates.

The dealuminated ZSM-5 preferably has a ratio of the average SAR at the edge of the crystallite to the average SAR at the center of the crystallite of greater than 1.15, more preferably at least 2, more preferably at least 3. The SAR in these cases is measured by elemental maps produced from energy dispersive X-ray spectroscopy (EDX) coupled with transmission electron microscopy (TEM).

Removing alumina from zeolite can be carried out in any way known to someone skilled in the art. For the present invention, it is preferred to treat the zeolite particles with a fluorine-containing salt.

Most preferably, the dealumination is performed by a process in which the zeolite is contacted with a solution of ammonium fluoride, more specifically a compound chosen from the group consisting of fluorosilicates and fluorotitanates, most preferably a compound chosen from the group of fluorosilicates. These processes are described in more detail in U.S. Pat. No. 4,753,910 A. Most preferably, the dealumination process comprises contacting the zeolite with a solution of a fluorosilicate salt wherein the fluorosilicate salt is represented by the formula:

$$(A)_{2/b}SiF_6$$

wherein 'A' is a metallic or non-metallic cation other than H+ having the valence 'b'. Examples of cations 'b' are alkylammonium, $NH_4^+$, $Mg^{++}$, $Li^+$, $Na^+$, $K^+$, $Ba^{++}$, $Cd^{++}$, $Cu^+$, $Ca^{++}$, $Cs^+$, $Fe^{++}$, $Co^{++}$, $Pb^{++}$, $Mn^{++}$, $Rb^+$, $Ag^+$, $Sr^{++}$, $Tl^+$, and $Zn^{++}$. Preferably 'A' is the ammonium cation.

The solution comprising the fluorosilicate salt preferably is an aqueous solution. The concentration of the salt preferably is at least 0.005 mole of fluorosilicate salt/l, more preferably at least 0.007, most preferably at least 0.01 mole of fluorosilicate salt/l. The concentration preferably is at most 0.5 mole of fluorosilicate salt/l, more preferably at most 0.3, most preferably at most 0.1 of fluorosilicate salt/l. Preferably, the weight ratio of fluorosilicate salt solution to zeolite is from 50:1 to 1:4 of fluorosilicate solution to zeolite. If the zeolite is present together with binder, the binder is not taken into account for these weight ratios.

The pH of the aqueous fluorosilicate containing solution preferably is between 2 and 8, more preferably between 3 and 7.

The zeolite material preferably is contacted with the fluorosilicate salt solution for of from 0.5 to 20 hours, more specifically of from 1 to 10 hours. The temperature preferably is of from 10 to 120° C., more specifically of from 20 to 100° C. The amount of fluorosilicate salt preferably is at least 0.002 moles of fluorosilicate salt per 100 grams of total amount of zeolite, more specifically at least 0.003, more specifically at least 0.004, more specifically at least 0.005 moles of fluorosilicate salt per 100 grams of total amount of zeolite. The amount preferably is at most 0.5 moles of fluorosilicate salt per 100 grams of total amount of zeolite, more preferably at most 0.3, more preferably at most 0.1 moles of fluorosilicate salt per 100 grams of total amount of zeolite. If the zeolite is present together with binder, the binder is not taken into account for these weight ratios.

The ZSM-5 of the subsequent catalyst preferably has not been subjected to selective removal of alumina.

Hence, in a preferred embodiment, the process of the present invention comprises contacting an alkylaromatic feedstock with
i) a first catalyst comprising a) a carrier which comprises of from 20 to 70 wt. % of a refractory oxide binder and of from 30 to 80 wt. % of dealuminated ZSM-5 having a crystallite size of from 500 to 10,000 nm and a silica to alumina molar ratio (SAR) in the range of from 20 to 100; b) an amount of from 0.001 to 5 wt. % of one or more metals chosen from the group consisting of Groups 6, 9 and 10; and optionally c) a metal chosen from Group 14 in an amount up to 0.5 wt. %, and
ii) a subsequent catalyst comprising a) a carrier which comprises of from 20 to 70 wt. % of a refractory oxide binder; of from 30 to 80 wt. % of ZSM-5 having a crystallite size of from 3 to 100 nm and a SAR in the range of from 20 to 200, wherein said ZSM-5 has not been subjected to selective removal of alumina; b) an amount of from 0.001 to 5 wt. % of one or more metals chosen from the group consisting of Groups 6, 9 and 10; and optionally c) a metal chosen from Group 14 in an amount up to 0.5 wt. %, all percentages being on the basis of total catalyst.

The average SAR at the edge of the crystallite of the ZSM-5 of the subsequent catalyst preferably is substantially the same as the average SAR at the center of this crystallite. Preferably, the ratio of the average SAR at the edge of the crystallite to the average SAR at the center of the crystallite of the ZSM-5 of the subsequent catalyst is of from 0.80 to 1.10, more specifically this ratio is 1.

The ZSM-5 of the subsequent catalyst preferably has a mesopore volume of at least 0.10 ml/g, more specifically at least 0.15 ml/g, most specifically at least 0.20 ml/g. The mesopore volume of the ZSM-5 of the subsequent catalyst preferably is at most 1.0 ml/g, more specifically at most 0.90 ml/g, more specifically at most 0.80 ml/g, more specifically at most 0.70 ml/g, more specifically at most 0.60 ml/g, more specifically at most 0.50 ml/g, most specifically at most 0.40 ml/g. The mesopores, as the term is used herein, are those pores of the zeolite having a pore diameter in the range of from 50 to 350 angstroms (Å). These are measured according to ASTM D4365-13.

The macropore volume of ZSM-5 of the subsequent catalyst preferably is at least 0.3 ml/g, more specifically at least 0.4 ml/g, most specifically at least 0.5 ml/g. The macropore volume of the catalyst preferably is at most 1.5 ml/g, more specifically at most 1.0 ml/g.

The macropores are the pores of the catalyst having a pore diameter greater than 350 Å, more specifically of from 350 to 2000 Å. These are measured according to ASTM D4284.

The micropore volume of the ZSM-5 of the subsequent catalyst preferably is at least 0.01 ml/g, more specifically at least 0.02 ml/g. The micropore volume of this ZSM-5 preferably is at most 0.09 ml/g, more specifically at most 0.08 ml/g, most specifically at most 0.06 ml/g. The micropores, as the term is used herein, are those pores of the catalyst having a pore diameter less than 50 angstroms (Å). These are measured according to ASTM D4222-03.

The crystallite size of the ZSM-5 of the subsequent catalyst preferably is at least 3 nm, more specifically at least 5 nm, more specifically at least 10 nm, more specifically at least 20 nm. The crystallite size of the ZSM-5 of the subsequent catalyst preferably is at most 100 nm, more specifically at most 90 nm, more specifically at most 80 nm, more specifically at most 70 nm, more specifically at most 60 nm, more specifically at most 50 nm, most specifically at most 40 nm.

The silica to alumina molar ratio of the ZSM-5 of the subsequent catalyst preferably is at least 20, more specifically at least 30, more specifically at least 40, most specifically at least 50. This ratio preferably is at most 180, more specifically at most 150, more specifically at most 120, most specifically at most 110.

The subsequent catalyst most preferably contains ZSM-5 which is commercially available from Zeolyst under the trade name "ZD13008".

The binder of each the first and the subsequent catalyst is a refractory oxide. Refractory oxides which can be used include alumina, silica-alumina, aluminum phosphate, silica, zirconia and titania. It will be obvious that it is preferred that no alumina is present during dealumination of the ZSM-5 of the first catalyst. This can be achieved by dealuminating ZSM-5 for the first catalyst before adding alumina containing binder. Preferably, the refractory oxide of the first catalyst is selected from the group consisting of silica, zirconia and titania. The binder for the subsequent catalyst preferably is selected from the group consisting of silica, zirconia, alumina, silica-alumina and aluminum phosphate.

Most preferably, silica is used as a binder in each the first and the subsequent catalyst. The silica may be naturally occurring silica or may be in the form of a gelatinous precipitate, sol or gel. The form of silica is not limited and the silica may be in any of its various forms: crystalline silica, vitreous silica or amorphous silica. The term amorphous silica encompasses the wet process types, including precipitated silicas and silica gels, or pyrogenic or fumed silicas. Silica sols or colloidal silicas are non-settling dispersions of amorphous silicas in a liquid, usually water, typically stabilized by anions, cations, or non-ionic materials.

The silica binder preferably is a mixture of two silica types, most preferably a mixture of a powder form silica and a silica sol. Conveniently powder form silica has a B.E.T. surface area in the range of from 50 to 1000 $m^2/g$; and a mean particle size in the range of from 2 nm to 200 micron m, preferably in the range of from 2 to 100 micron m, more preferably 2 to 60 micron m, especially 2 to 10 micron m as measured by ASTM C 690-1992 or ISO 8130-1. A very suitable powder form silica material is "Sipernat 50", a white silica powder having predominantly spherical particles, available from Degussa ("Sipernat" is a trade name). A very suitable silica sol is that sold under the trade name of "Bindzil" by Eka Chemicals. Where the mixture comprises powder form silica and a silica sol, then the two components may be present in a weight ratio of powder form to sol form in the range of from 1:1 to 10:1, preferably 2:1 to 5:1, more preferably from 2:1 to 3:1. The binder may also consist essentially of just the powder form silica.

Where solely a powder form of silica is used as a binder in the catalyst composition of the present invention, preferably a small particulate form is utilized, which has a mean particle size in the range of from 2 to 10 micron as measured by ASTM C 690-1992. An additional improvement in carrier strength is found with such materials. A very suitable small particulate form is that available from Degussa under the trade name "Sipernat 500LS".

Preferably the silica component is used as pure silica and not in combination with other refractory oxide components. It is most preferred that the silica and indeed the carrier, is essentially free of any other inorganic oxide binder material, and especially is free of alumina. At most only a maximum of 2 wt. % alumina, based on the total refractory oxide binder, is present.

The carrier of the first catalyst preferably comprises of from 20 to 70 wt. % of binder in combination with of from 30 to 80 wt. % of dealuminated ZSM-5, more specifically of from 25 to 60 wt. % of binder in combination with of from 40 to 75 wt. % of dealuminated ZSM-5, more specifically of from 25 to 65 wt. % of binder in combination with of from 30 to 75 wt. % of dealuminated ZSM-5, most specifically 30 to 50 wt. % of binder in combination with of from 50 to 70 wt. % of dealuminated ZSM-5.

The subsequent catalyst preferably comprises of from 20 to 70 wt. % of binder in combination with of from 30 to 80 wt. % of ZSM-5, more specifically of from 25 to 60 wt. % of binder in combination with of from 40 to 75 wt. % of ZSM-5, more specifically of from 25 to 65 wt. % of binder in combination with of from 30 to 75 wt. % of ZSM-5, most specifically 30 to 50 wt. % of binder in combination with of from 50 to 70 wt. % of ZSM-5.

The ZSM-5 and refractory oxide binder for each the first and the subsequent catalyst may be shaped into any convenient form such as powders, extrudates, pills and granules. Preference is given to shaping by extrusion. To prepare extrudates, commonly the pentasil zeolite will be combined with the binder, preferably silica, and if necessary a peptizing agent, and mixed to form a dough or thick paste. The peptizing agent may be any material that will change the pH of the mixture sufficiently to induce deagglomeration of the solid particles. Peptising agents are well known and encompass organic and inorganic acids, such as nitric acid, and alkaline materials such as ammonia, ammonium hydroxide, alkali metal hydroxides, preferably sodium hydroxide and potassium hydroxide, alkali earth hydroxides and organic amines, e.g. methylamine and ethylamine. Ammonia is a preferred peptizing agent and may be provided in any suitable form, for example via an ammonia precursor. Examples of ammonia precursors are ammonium hydroxide and urea. It is also possible for the ammonia to be present as part of the silica component, particularly where a silica sol is used, though additional ammonia may still be needed to impart the appropriate pH change. The amount of ammonia present during extrusion has been found to affect the pore structure of the extrudates which may provide advantageous properties. Suitably the amount of ammonia present during extrusion may be in the range of from 0 to 5 wt. % based on the total dry mixture, preferably 0 to 3 wt. %, more preferably 0 to 1.9 wt. %, on dry basis.

The ZSM-5 present in each of the first catalyst and the subsequent catalyst has physical characteristics similar to those of the ZSM-5 used as starting compound in their preparation. Therefore, the preferences for physical properties of ZSM-5 which is part of catalyst also apply to ZSM-5 used in preparing the catalyst.

The first and the subsequent catalyst each comprise of from 0.001 to 5 wt. % of one or more metals chosen from the group consisting of Groups 6, 9 and 10 and optionally a metal chosen from Group 14 in an amount up to 0.5 wt. %, on the basis of total catalyst. Preferably, the metal of Group 6, 9 or 10 is chosen from the group consisting of tungsten, molybdenum, cobalt, nickel, palladium and platinum while the metal of Group 14 is chosen from lead and tin. Most preferably, the catalyst comprises of from 0.001 to 0.1 wt. % of platinum and/or palladium, most preferably platinum, based on amount of metal on total amount of catalyst. The amount preferably is from 0.01 to 0.05 wt. %. Additionally, each the first and the subsequent catalyst can contain one or more further catalytically active compounds, most preferably tin.

The metals emplacement onto the carrier may be by methods usual in the art. The metals can be deposited onto the carrier prior to shaping, but it is preferred to deposit them onto a shaped carrier.

Pore volume impregnation of the metals from a metal salt solution is a very suitable method of metals emplacement onto a shaped carrier. The metal salt solutions may have a pH in the range of from 1 to 12. The platinum salts that may conveniently be used are chloroplatinic acid and ammonium stabilized platinum salts. If tin is present, the tin preferably is added as a salt selected from the group consisting of stannous (II) chloride, stannic (IV) chloride, stannous sulphate, and stannous acetate.

If different metals are deposited on the carrier, the metals may be impregnated onto the shaped carrier either sequentially or simultaneously. Where simultaneous impregnation is utilized the metal salts used must be compatible and not hinder the deposition of the metals. It has been found useful to utilize a complexing or chelating agent in a combined platinum/tin salt solution to prevent unwanted metals precipitation. Examples of suitable complexing agents are EDTA (ethylenediamine tetraacetic acid), and derivatives thereof, HEDTA (N-(2-hydroxyethyl) ethylenediamine-N, N',N'-triacetic acid), EGTA (ethylene glycol-bis(2-aminoethylether)-N,N,N',N'-tetraacetic acid), DTPA (diethylene tridiamine pentaacetic acid), and NTA (nitrilotriacetic acid). Where EDTA is used, it is conveniently used in a molar ratio to tin of from 0.1 to 3, especially 1 to 2.

After shaping of the carrier, and also after metals impregnation, the carrier/catalyst is suitably dried, and calcined. Drying temperatures are suitably 50 to 200° C.; drying times are suitably from 0.5 to 5 hours. Calcination temperatures are very suitably in the range of from 200 to 800° C., preferably 300 to 600° C. For calcination of the carrier, a relatively short time period is required, for example 0.5 to 3 hours. For calcination of the catalyst composition, it may be necessary to employ controlled temperature ramping at a low rate of heating to ensure the optimum dispersion of the metals. Such calcination may require from 5 to 20 hours.

Prior to use, it is generally necessary to ensure that the metals on the catalyst composition are in metallic (and not oxidic) form. Accordingly, it is useful to subject the composition to reducing conditions, which are, for example, heating in a reducing atmosphere, such as in hydrogen optionally diluted with an inert gas, or mixture of inert gases, such as nitrogen and carbon dioxide, at a temperature in the range of from 150 to 600° C. for from 0.5 to 5 hours.

Preferably, the weight ratio of first catalyst to subsequent catalyst is of from 1:9 to 9:1, more specifically of from 1:8 to 8:1, more specifically of from 1:7 to 7:1, more specifically of from 1:5 to 5:1, most specifically of from 1:3 to 3:1.

The feedstock for use in the present process most suitably originates directly from a reforming unit or naphtha pyrolysis unit or is the effluent of a xylene isomerisation unit. Such feedstock usually comprises hydrocarbons containing of from 7 to 9 carbon atoms, and in particular, one or more of o-xylene, m-xylene, p-xylene, toluene, and benzene in addition to ethylbenzene. Typically, the xylenes will not be in a thermodynamic equilibrium, and the content of p-xylene will accordingly be lower than that of the other isomers.

The feedstock preferably comprises ethylbenzene. Generally, the amount of ethylbenzene in the feedstock is in the range of from 0.1 to 50 wt. % and the total xylene content is typically of from 20 to 99.9 wt. %, each based on total amount of hydrocarbon feedstock. More specifically, the total xylene content is typically at least 30 wt. %.

The feedstock is contacted with the catalyst in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The process is suitably carried out at a temperature in the range of from 300 to 500° C., a pressure in the range of from 0.1 to 50 bar (10 to 5,000 kPa), using a weight hourly space velocity of in the range of from 0.5 to 20 g feed/g catalyst/hour. A partial pressure of hydrogen in the range of from 0.05 to 30 bar (5 to 3,000 kPa) is generally used. The feed to hydrogen molar ratio is in the range of from 0.5 to 100, generally from 1 to 10 mol/mol.

The present invention will now be illustrated by the following Examples.

EXAMPLES

Example 1 (Manufacture of Catalyst A)

92 g of solid sodium hydroxide and 125 g of L-tartaric acid were dissolved in 3.5 l of water to which was added 175 g of a sodium aluminate solution to prepare a homogeneous solution. Then, 660 g of silicic acid powder was added into this mixed solution slowly with stirring to prepare a homogeneously aqueous reaction mixture. The reaction mixture was placed in an autoclave and, after closing the autoclave, was allowed to react at 160° C. for 72 hours with stirring. Thereafter, the reaction product was taken out of the autoclave, washed with distilled water until its pH was almost neutral, then filtered and dried overnight at 120° C. The product thus obtained is ZSM-5 having the properties is shown in below Table 1. This zeolite is hereinafter referred to as Zeolite A.

TABLE 1

|  | Zeolite A |
| --- | --- |
| Molar silica to alumina ratio | 41 |
| Wt. % $Na_2O$ | 0.01 |
| BET Surface Area ($m^2/g$) | 438 |
| Micropore Volume (cc/g) | 0.155 |
| Mesopore Volume (cc/g) | 0.027 |
| Mesopore BET Surface Area ($m^2/g$) | 45 |
| Pore Volume Distribution (cc/g): |  |
| 260-600 Å | 0.005 |
| 100-260 Å | 0.003 |
| 50-100 Å | 0.002 |
| 20-50 Å | 0.018 |

The micropore and the mesopore volume each were derived from the nitrogen adsorption and desorption isotherm measured according to ASTM D4222-03. The mesopore BET surface area was measured according to ASTM D4365-13. The product obtained had a number average crystal size of 5000 nm (5 microns) as measured by Transmission Electron Microscopy (TEM).

Zeolite powder A was mixed with a low sodium grade silica ("Sipernat 50" from Degussa) and an ammonium stabilized commercially available silica sol (sold under the trade name "Bindzil 30NH3" by Eka Chemicals), and extruded to give a carrier comprised of 60 wt. % zeolite, 26.6 wt. % "Sipernat 50" and 13.4 wt. % silica sol on dry basis. The green extrudates were dried and calcined at 500° C. to achieve sufficient strength for industrial application. The resulting carrier is hereinafter referred to as Carrier A.

The carrier thus obtained was pore volume impregnated with a solution comprising both platinum and tin to obtain a final catalyst having a concentration of 0.025 wt. % of platinum and 0.4 wt. % of tin, each based on total catalyst. Once the impregnation was completed, the catalyst was dried and subsequently calcined. The catalyst obtained is hereinafter referred to as Catalyst A.

Scanning Electron Microscope (SEM) images showed that the zeolite particles in the catalyst are the same size as the zeolite per se.

Example 2 (Manufacture of Catalyst B)

A sample of Carrier A as described in Example 1 was subjected to dealumination by treating the sample with 0.02 M aqueous ammonium hexafluorosilicate solution. The thus treated sample was subsequently washed, dried and calcined.

The carrier thus obtained was pore volume impregnated with a solution containing platinum (but no tin) to obtain a final catalyst having a concentration of 0.025 wt. % of platinum, based on total catalyst. Once the impregnation was completed, the catalyst was dried and subsequently calcined. The catalyst obtained is hereinafter referred to as Catalyst B.

Example 3 (Manufacture of Catalyst C)

A carrier was prepared from ZSM-5 having a mesopore volume of 0.29 ml/g, a number average crystallite size of 28 nm and a silica to alumina molar ratio of 80. This ZSM-5 is commercially available from Zeolyst as "ZD 13008" and is hereinafter referred to as Zeolite C. A high mesopore volume in the zeolite translates into a high mesopore volume of the zeolite in the catalyst.

The zeolite powder was mixed with a low sodium grade silica ("Sipernat 50" from Degussa), and an ammonium stabilized commercially available silica sol (sold under the trade name "Bindzil 30NH3" by Eka Chemicals), and extruded to give a carrier comprised of 60 wt. % zeolite, 26.6 wt. % "Sipernat 50" and 13.4 wt. % silica sol on dry basis.

The green extrudates were dried and calcined at 500° C. to achieve sufficient strength for industrial application. The resulting carrier is hereinafter referred to as Carrier C.

The carrier was pore volume impregnated with a platinum containing solution. The concentration of metal was such as to provide a final catalyst having a concentration of 0.025 wt. % of platinum, based on total catalyst. Once the impregnation was completed, the catalyst was dried and subsequently calcined. This catalyst is hereinafter referred to as Catalyst C.

Example 4 (Manufacture of Catalyst D)

A sample of Carrier C as described in Example 3 was subjected to dealumination by treating the sample with 0.02 M aqueous ammonium hexafluorosilicate solution. The thus treated sample was subsequently washed, dried and calcined.

The carrier thus obtained was pore volume impregnated with a solution containing platinum to obtain a final catalyst having a concentration of 0.025 wt. % of platinum, based on total catalyst. Once the impregnation was completed, the catalyst was dried and subsequently calcined. The catalyst obtained is hereinafter referred to as Catalyst D.

Example 5 (Manufacture of Catalyst E)

A carrier was prepared by mixing 28 wt. % of Zeolite A as described in Example 1, 32 wt. % of Zeolite C as described in Example 3 and 40 wt. % of silica binder (26.6 wt. % "Sipernat 50" from Degussa and 13.4 wt. % "Bindzil 30NH3" by Eka Chemicals) and subsequently extruding the mixture. The green extrudates were dried and calcined at 500° C. to achieve sufficient strength for industrial application.

The carrier obtained was subjected to dealumination by treating the sample with 0.02 M aqueous ammonium hexafluorosilicate solution. The thus treated sample was subsequently washed, dried and calcined.

The carrier thus obtained was pore volume impregnated with a solution comprising both platinum and tin to obtain a final catalyst having a concentration of 0.025 wt. % of platinum and 0.4 wt. % of tin, each based on total catalyst. Once the impregnation was completed, the catalyst was dried and subsequently calcined. The catalyst obtained is hereinafter referred to as Catalyst E.

Example 6

Table 2 summarises the catalysts tested in Example 6.

Tests A-E were conducted using Catalysts A-E, respectively. Said tests are comparative in nature.

Test F utilised Catalysts B and C in a 50/50 weight ratio. The catalysts were loaded in a stacked-bed configuration: 50 parts per weight of Catalyst C was loaded in a fixed-bed reactor, topped by 50 parts per weight of Catalyst B. The reactor flow went from top to bottom of the reactor. Said test is in accordance with the present invention.

TABLE 2

| Test | Catalyst | Zeolite Type | Zeolite Crystallite Size (nm) | Zeolite Silica to Alumina Ratio (SAR) | Zeolite (wt. %) in Carrier | Carrier Dopants Pt (wt. %) | Sn (wt. %) | Zeolite Dealuminated? |
|---|---|---|---|---|---|---|---|---|
| A | A | A | 5000 | 41 | 60 | 0.025 | 0.4 | No |
| B | B | A | 5000 | 41 | 60 | 0.025 | — | Yes |
| C | C | C | 28 | 80 | 60 | 0.025 | — | No |
| D | D | C | 28 | 80 | 60 | 0.025 | — | Yes |
| E | E | (A + C)* | 5000 (Zeolite A) 28 (Zeolite C) | 41 (Zeolite A) 80 (Zeolite C) | 60** | 0.025 | 0.4 | Yes |
| F | | | Testing conduced using a combination of Catalyst B and Catalyst C. | | | | | |

*Catalyst made from physical mixture of zeolites.
**Composed of 32 wt. % Zeolite C and 28 wt. % Zeolite A to total 60 wt. % in Carrier.

Tests A-F were conducted under catalytic testing conditions that mimics typical industrial application conditions for ethylbenzene dealkylation. This activity test uses a feed having the composition summarized in Table 3.

TABLE 3

Composition of the feed used in the activity testing

| Component | (wt. % in feed composition) |
|---|---|
| Ethylbenzene (EB) | 15.30 |
| p-Xylene (pX) | 2.71 |
| o-Xylene (oX) | 15.62 |
| m-Xylene (mX) | 63.26 |
| Toluene | 0.28 |
| Benzene | 0.02 |
| C7-C8-naphthenes | 2.81 |
| C9+ aromatics | 0.00 |
| Total | 100.00 |

Other Feed Characteristics

| C8 aromatics sum (wt. %) | 96.89 |
|---|---|
| EB in C8 aromatics feed (wt. %) | 15.79 |

TABLE 3-continued

Composition of the feed used in the activity testing

| Component | (wt. % in feed composition) |
|---|---|
| pX (wt. %) in xylenes in feed | 3.33 |
| oX (wt. %) in xylenes in feed | 19.14 |
| mX (wt. %) in xylenes in feed | 77.53 |

The activity test is performed once the catalyst is in its reduced state, which is achieved by exposing the dried and calcined catalyst to atmospheric hydrogen (>99% purity) at 450° C. for 1 hour.

After reduction, the reactor is pressurized without a cooling step, and the feed is introduced. This step contributes to enhanced catalyst aging, and therefore allows comparison of the catalytic performance at stable operation.

The catalytic data points are collected at a condition that exaggerates the potential negative operational effects. Therefore, the performance is measured not at the ideal industrial operating conditions but at those that allow a better differentiation of the various performance parameters used to evaluate catalysts in this application.

In the present case, a weight hourly space velocity of 12 g feed/g catalyst/hour, hydrogen to feed ratio of 2.5 mol·mol$^{-1}$ and a total system pressure of 1.2 MPa was used. The temperature was varied between 340 and 380° C. to achieve the required conversion for easier comparison.

The performance characteristics including the product obtained are shown in Table 4 below.

Ethylbenzene conversion (EB conversion) is the weight percent of ethylbenzene converted by the catalyst into benzene and ethylene, or other molecules. It is defined as wt. % ethylbenzene in feed minutes wt. % ethylbenzene in product divided by wt. % ethylbenzene in feed times 100%.

PXate is a measure for the degree to which the xylene reaction mixture has reached equilibrium for para-xylene. It is defined as follows:

$$PXate = \frac{\text{wt. \% } pX \text{ in Xylenes in product} - \text{wt. \% } pX \text{ in Xylenes in feed}}{\text{wt. \% } pX \text{ in Xylenes at equilibrium} - \text{wt. \% } pX \text{ in Xylenes in feed}} \times 100\%$$

where pX stands for para-xylene.

Xylene loss is calculated as wt. % xylenes in feed minus wt. % xylenes in product divided by wt. % xylenes in feed times 100%.

TABLE 4

| Catalyst | A | B | C | D | E | B and C in a 50/50 weight ratio |
|---|---|---|---|---|---|---|
| EB conversion, wt. % | 65 | 65 | 65 | 65 | 65 | 65 |
| PXate, % | 96.5 | 85.8 | 102.1 | 101.9 | 101.8 | 102.1 |
| Xylene loss, wt. % | 3.41 | 1.71 | 2.11 | 2.85 | 2.27 | 1.95 |
| Para-Xylene (pX) in product, wt. % | 18.08 | 16.76 | 19.20 | 18.95 | 19.13 | 19.40 |

The above experimental results show that the combination of catalysts according to the present invention (Catalyst F) allows to dealkylate an alkylaromatics feedstock while simultaneously isomerizing xylene such that a product is obtained which is relatively high in para-xylene.

The results obtained for Test F, utilizing a combination of catalysts as described in the present invention, are better than the results obtained in Tests A-E for various single catalysts (Catalysts A-D) and are also better than for Catalyst E which utilized a mixture of zeolites in its preparation.

That which is claimed is:

1. A process for dealkylation of alkylaromatic compounds, which process comprises:
    (a) contacting under dealkylation conditions an alkylaromatic feedstock with a first catalyst and a subsequent catalyst, which catalysts are loaded within a reactor in a stacked-bed configuration with the first catalyst loaded on top of the subsequent catalyst at a weight ratio of the first catalyst to the subsequent catalyst of from 1:9 to 9:1, wherein the alkylaromatic feedstock flows from a top to a bottom of the reactor, and wherein
        i) the first catalyst comprises a) a carrier which comprises from 20 to 70 wt. % of a refractory oxide binder and from 30 to 80 wt. % of dealuminated ZSM-5 having a crystallite size of from 500 to 10,000 nm and a silica to alumina molar ratio (SAR) in a range of from 20 to 100; and b) platinum in an amount from 0.001 to 5 wt. %, based on a total weight of the first catalyst; and
        ii) the subsequent catalyst comprises a) a carrier which comprises from 20 to 70 wt. % of a refractory oxide binder; and from 30 to 80 wt. % of ZSM-5 having a crystallite size of from 3 to 100 nm and a SAR in a range of from 20 to 200, wherein the ZSM-5 of the subsequent catalyst has not been subjected to selective removal of alumina; and b) platinum in an amount of from 0.001 to 5 wt. %, based on a total weight of the subsequent catalyst; and
    (b) producing a product stream comprising a dealkylated aromatic compound.

2. The process as claimed in claim 1, wherein the ZSM-5 of the subsequent catalyst has a mesopore volume of from 0.1 to 1.0 ml/g.

3. The process as claimed in claim 1, wherein the dealuminated ZSM-5 of the first catalyst has a ratio of the average SAR at an edge of a crystallite to the average SAR at the center of the crystallite of greater than 1.15.

4. The process as claimed in claim 1, wherein the dealuminated ZSM-5 of the first catalyst has a crystallite size of from 1,000 to 10,000 nm.

5. The process as claimed in claim 1, wherein the ZSM-5 of the subsequent catalyst has a crystallite size of from 5 to 80 nm.

6. The process as claimed in claim 1, wherein the weight ratio of the first catalyst to the subsequent catalyst is from 1:5 to 5:1.

7. The process as claimed in claim 1, wherein the alkylaromatic feedstock comprises ethylbenzene.

8. The process as claimed in claim 7, wherein the alkylaromatic feedstock comprises in a range of from 0.1 to 50 wt. % of ethylbenzene and in a range of from 20 to 99.9 wt. % of xylene, based on a total amount of the alkylaromatic feedstock.

* * * * *